(12) United States Patent
Nozawa et al.

(10) Patent No.: US 7,784,948 B2
(45) Date of Patent: Aug. 31, 2010

(54) VISUAL ACUITY TESTING APPARATUS

(75) Inventors: Noritsugu Nozawa, Toyokawa (JP);
Yuichiro Kanazawa, Okazaki (JP);
Ryoji Suzuki, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 247 days.

(21) Appl. No.: 12/081,479

(22) Filed: Apr. 16, 2008

(65) Prior Publication Data
US 2008/0259278 A1 Oct. 23, 2008

(30) Foreign Application Priority Data
Apr. 20, 2007 (JP) ............................. 2007-112423

(51) Int. Cl.
*A61B 3/10* (2006.01)
(52) U.S. Cl. ...................... 351/211; 351/243
(58) Field of Classification Search ................. 351/211
See application file for complete search history.

(56) References Cited

U.S. PATENT DOCUMENTS

| 1,698,013 | A | | 1/1929 | De Zeng |
| 3,490,832 | A | | 1/1970 | Mitsuishi et al. |
| 3,947,098 | A | | 3/1976 | Paget |
| 3,969,020 | A | | 7/1976 | Lynn et al. |
| 4,105,302 | A | * | 8/1978 | Tate, Jr. ....................... 351/210 |
| 4,953,968 | A | * | 9/1990 | Sherwin et al. ............. 351/211 |
| 5,078,486 | A | | 1/1992 | Evans |

FOREIGN PATENT DOCUMENTS

| DE | 70 08 479 U | 8/1971 |
| FR | 2 235 627 A | 1/1975 |
| JP | A 50-37293 | 4/1975 |
| JP | A 6-285022 | 10/1994 |
| JP | A 2003-310552 | 11/2003 |

* cited by examiner

*Primary Examiner*—Jordan M. Schwartz
*Assistant Examiner*—James C Jones
(74) *Attorney, Agent, or Firm*—Oliff & Berridge, PLC

(57) ABSTRACT

A visual acuity testing apparatus capable of performing visual acuity testing under substantially uniform conditions even when a test distance and an installation distance vary has a projection optical unit including a disk whereon a chart is placed, an illumination light source, and variable projection lenses which are moved so as to change an image-forming position and an image size of an image of the chart, an input unit into which an installation distance between the screen and the visual acuity testing apparatus and a test distance between the screen and an examinee are inputted, a projection lens driving unit which moves the variable projection lenses based on the installation distance and the test distance, and a light intensity adjusting unit which adjusts light intensity based on the installation distance and the test distance so that brightness of the chart image falls within a predetermined reference range.

6 Claims, 3 Drawing Sheets

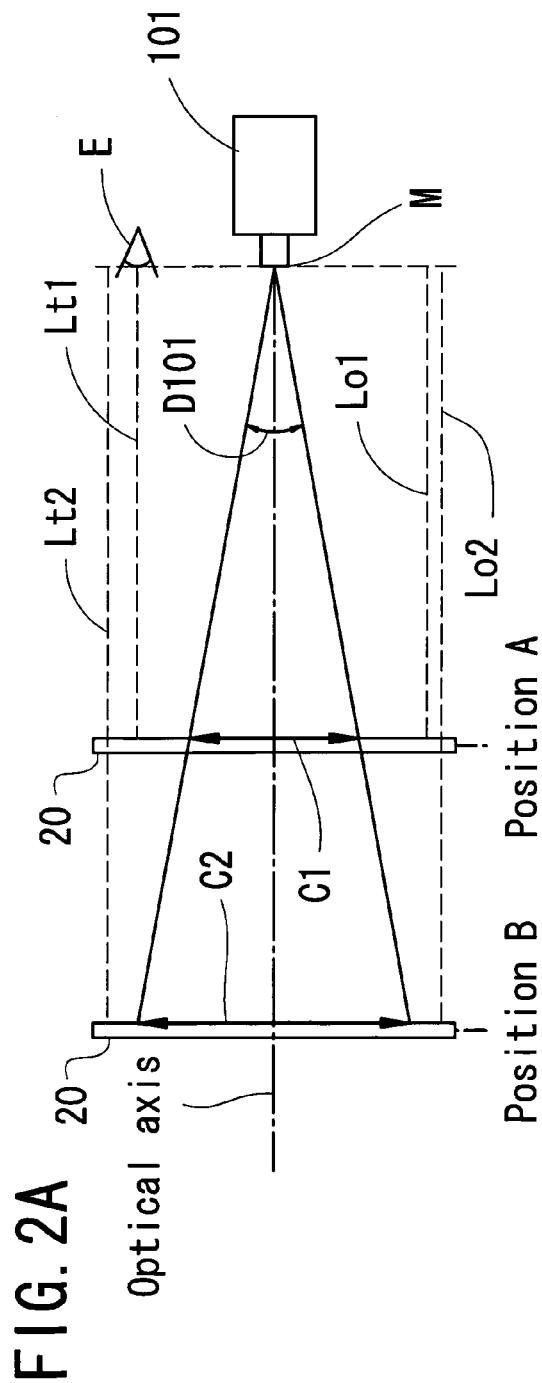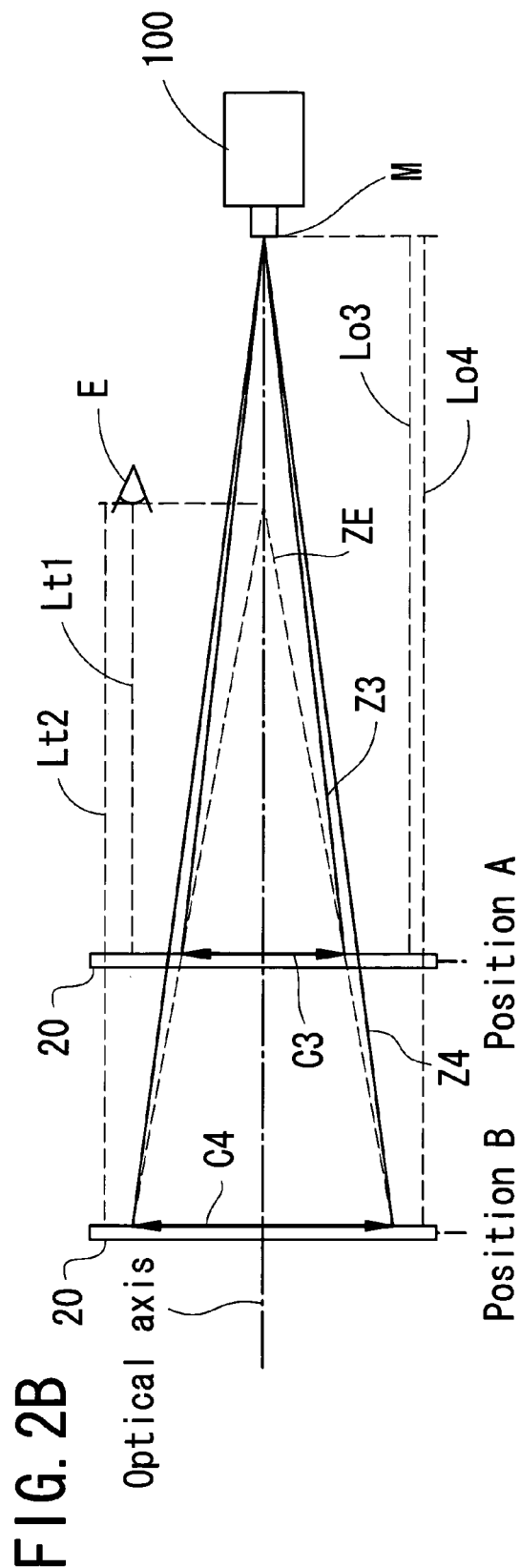

| Current value of white LED [mA] | Installation distance [m] | | | | | | |
|---|---|---|---|---|---|---|---|
| | | 3 | 3.5 | 4 | 4.5 | 5 | 5.5 | 6 |
| Test distance [m] | 3 | *** | *** | *** | *** | *** | *** | *** |
| | 3.5 | *** | *** | *** | *** | *** | *** | *** |
| | 4 | *** | *** | *** | *** | *** | *** | *** |
| | 4.5 | *** | *** | *** | *** | *** | *** | *** |
| | 5 | *** | *** | *** | *** | *** | *** | *** |
| | 5.5 | *** | *** | *** | *** | *** | *** | *** |
| | 6 | *** | *** | *** | *** | *** | *** | *** |

FIG. 3

VISUAL ACUITY TESTING APPARATUS

BACKGROUND OF THE INVENTION

1. Field of the Invention

The present invention relates to a visual acuity testing apparatus which projects an image of a chart for visual acuity testing onto a screen and tests visual acuity of an examinee's eye.

2. Description of Related Art

Conventionally, there is known a projection-type visual acuity testing apparatus which projects an image of a chart for visual acuity testing onto a screen placed in a position at a predetermined distance (a test distance) from an examinee. In this apparatus, a projection lens is moved in accordance with positions of the screen, the apparatus, and the examinee. In one type of the apparatus, an installation distance (a distance from the screen to the apparatus, also called as a projection distance) and the test distance are equal, and an adjustment is performed so that an image of the chart having a predetermined size corresponding to these distances is projected onto the screen (see Japanese Patent Application Unexamined Publication No. 2003-310552 (hereinafter referred to as patent document 1)). The scheme of patent document 1 is called a fixed power scheme. Meanwhile, in another type of the apparatus, the size of an image of the chart projected onto a screen can be zoomed in or out by moving a plurality of projection lenses (see U.S. Pat. No. 3,947,098 corresponding to Japanese Patent Application Unexamined Publication No. Sho50-37293 (hereinafter referred to as patent document 2)). The scheme of patent document 2 is called a variable power scheme.

In the apparatus using the fixed power scheme, the size of the chart image projected onto the screen is uniquely determined in accordance with the installation distance and the test distance. Additionally, projection light intensity of the chart image projected onto the screen is adjusted in accordance with the installation distance and the test distance. This adjustment is performed so that the examinee perceives that brightness of the chart image is substantially constant at a reference value.

Meanwhile, in the apparatus using the variable power scheme, the installation distance and the test distance are not necessarily required to be equal. In other words, the installation distance and the test distance can be set independently. The size of the chart image projected onto the screen is determined in accordance with the set installation distance and test distance. Projection light intensity of the chart images is not adjusted in any conventional apparatuses using the variable power scheme.

As an allowable range of the international standard for brightness of chart images is relatively wide, no problems are particularly indicated regarding the foregoing apparatus (which is incapable of adjusting the projection light intensity of the chart images). However, when the test distance and the installation distance vary, the brightness of the chart image varies. This means that tests are performed under different conditions, thereby possibly influencing test results.

SUMMARY OF THE INVENTION

An object of the invention is to overcome the problems described above and to provide a visual acuity testing apparatus capable of performing visual acuity testing under substantially uniform conditions even when a test distance and an installation distance vary in an apparatus using the variable power scheme.

To achieve the objects and in accordance with the purpose of the present invention, a visual acuity testing apparatus which projects an image of a chart for visual acuity testing onto a screen has a projection optical unit including a disk whereon the chart is placed, an illumination light source, and variable projection lenses which include a plurality of projection lenses movable in a direction of an optical axis which are moved so as to change an image-forming position and an image size of the chart image, an input unit in to which an installation distance which defines a distance between the screen and the visual acuity testing apparatus and a test distance which defines a distance between the screen and an examinee are inputted, a projection lens driving unit which moves the variable projection lenses based on the installation distance and the test distance inputted into the input unit, and a light intensity adjusting unit which adjusts light intensity based on the installation distance and the test distance so that brightness of the chart image falls within a predetermined reference range.

Additional objects and advantages of the invention are set forth in the description which follows, are obvious from the description, or may be learned by practicing the invention. The objects and advantages of the invention may be realized and attained by the visual acuity testing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 2A and 2B are schematic views illustrating projection of chart images by an projection-type visual acuity testing apparatus using a fixed power scheme, and projection of chart images by an projection-type visual acuity testing apparatus using a variable power scheme according the preferred embodiment of the present invention; and FIG. 3 is a table indicating correspondence of current values of an illumination light source 1 to an installation distance and a test distance.

DETAILED DESCRIPTION OF THE PREFERRED EMBODIMENTS

Figure 1:
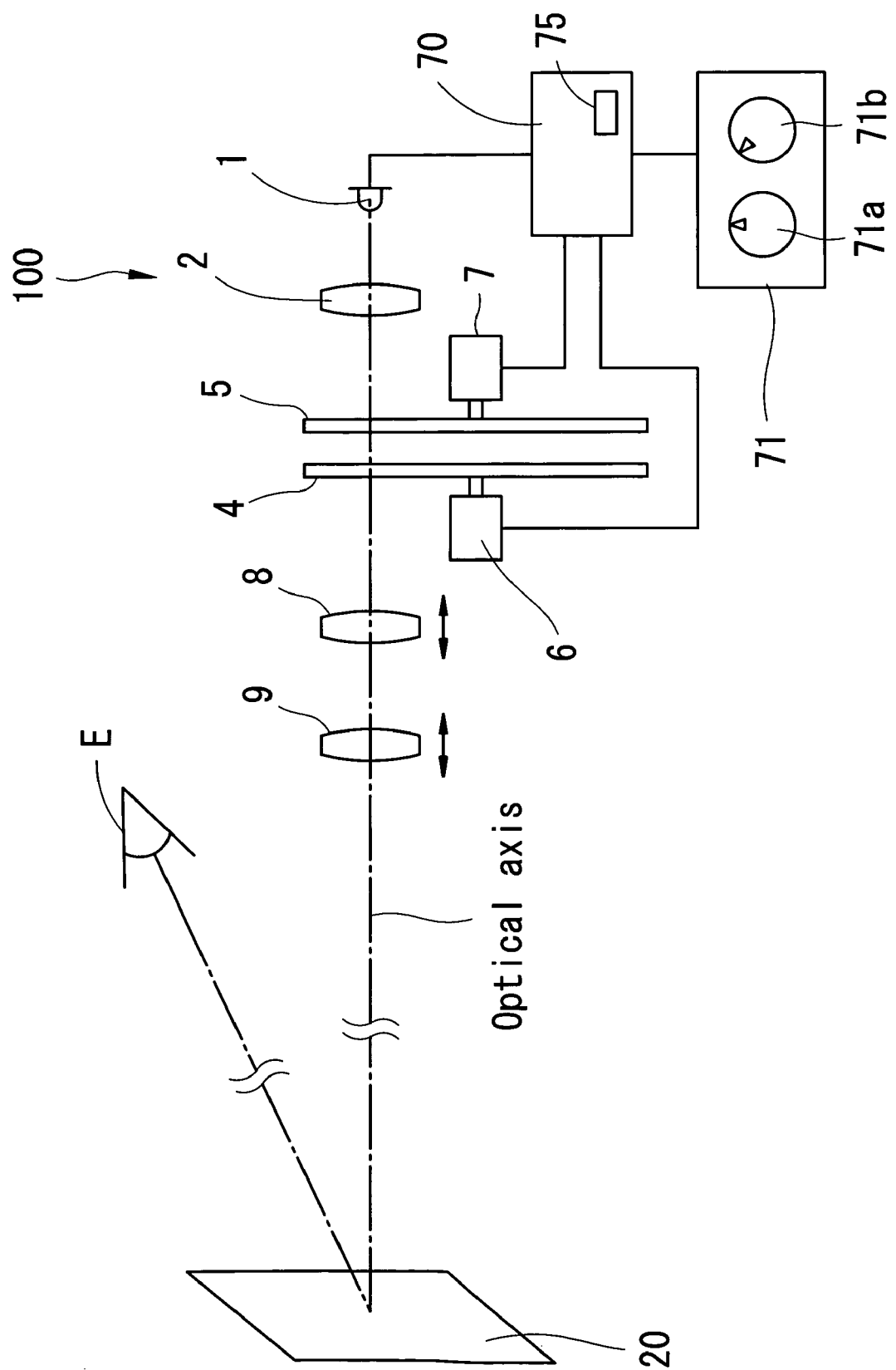
FIG. 1 is a schematic view showing a configuration of an optical system and a control system of a projection-type visual acuity testing apparatus according to a preferred embodiment of the present invention.

A detailed description of a visual acuity testing apparatus according to preferred embodiments of the present invention is provided below with reference to the accompanying drawings. FIG. 1 is a schematic view showing a configuration of an optical system and a control system of a projection-type visual acuity testing apparatus (a projection-type chart presenting apparatus) 100.

A white LED is used as an illumination light source 1. Between a condenser lens 2 and projection lenses 8 and 9, placed are a chart disk 4 and a mask disk 5. The chart disk 4 is a disk plate made of a transparent material such as glass. On a circumference of a circle on the chart disk 4, a plurality of charts is formed by chrome deposition. The charts are illuminated from behind by the illumination light source 1 via the condenser lens 2. The chart disk 4 is rotated by a motor 6, thereby changing types of the charts. The mask disk 5 is used to provide masks such as a vertical line mask, a horizontal line mark, and a single letter mask, to the charts. The mask disk 5 is rotated by a motor 7, thereby changing types of the masks. A screen 20 is placed at a distance of 3 to 6 mm from the apparatus 100 (details of the installation distance are described later).

A light bundle emitted from the illumination light source 1 converges at the condenser lens 2 and illuminates the mask disk 5 and the chart disk 4. A chart is illuminated via the mask disk 5 and an image of the chart is projected onto the screen 20 by the projection lenses 8 and 9 so as to be presented to an examinee's eye E. The condenser lens 2 and the projection lenses 8 and 9 are housed in a cylindrical member (not shown). The projection lenses 8 and 9 are independently movable along an optical axis inside the cylindrical member (see arrows in the FIG. 1 for moving directions). Positions of the projection lenses 8 and 9 can also be fixed using screws or others. By moving the projection lenses 8 and 9 on the optical axis, the size of the chart image is adjusted to a predetermined size. The foregoing parts are included in a chart projection optical system (a chart projection optical unit).

The chart projection optical system is not limited to the preferred embodiment of the present invention. For example, used may be a chart projection optical system which can zoom in or out a chart image projected onto a screen by using an optical element such as a variable-focal lens, which can singly change reflective power.

A control unit (controller) 70 controls to send signals to the motors 6 and 7 and rotates the chart disk 4 and the mask disk 5 so as to place an intended chart on the optical axis. The control unit 70 is connected with an operating unit (not shown). The operating unit controls to perform operations such as a changeover between the charts. In addition, a current control circuit is incorporated in the control unit 70. The current control circuit changes an amount of a current to be supplied to the illumination light source 1. Light intensity of the illumination light source 1 is changed (adjusted) in accordance with the amount of the current.

A set value of an installation distance (projection distance) between the screen 20 and the apparatus 100 and a set value of a test distance between the screen 20 and the examinee (eye E) are inputted by a distance setting unit (input means (an input unit)) 71. The distance setting unit 71 comprises an installation distance setting knob 71*a* and a test distance setting knob 71*b*. Both the knobs 71 and 72 are calibrated in distance. By rotating the knobs 71*a* and 71*b*, the installation distance and the test distance are set respectively. Based on the set installation distance and test distance, the control unit 70 controls to change the light intensity of the illumination light source 1 so that brightness of the chart image (hereinafter referred to as chart brightness) projected onto the screen 20 conforms to the standard (requirements) of visual acuity testing.

The control unit 70 and the distance setting unit 71 described above are included in adjustment means (an adjustment unit) which adjusts the light intensity (projection light intensity of the chart image projection) of the illumination light source 1.

A description of how to adjust the size of the chart image on the screen 20 in accordance with the installation distance and the test distance of the projection-type visual acuity testing apparatus is provided below. FIGS. 2A and 2B are schematic views illustrating projection of chart images by a projection-type visual acuity testing apparatus 101 using a fixed power scheme, and projection of chart images by the projection-type visual acuity testing apparatus 100 using a variable power scheme according to the preferred embodiment of the present invention. The screen 20 is placed in a position A or a position B, and distances from the eye E to the screens 20 placed in the position A and the position B are test distances Lt1 and Lt2 respectively. The apparatus 101 is placed at an installation distance Lo1 or Lo2 from the screen 20 placed in the position A or the position B. The apparatus 100 is placed at an installation distance Lo3 or Lo4 from the screen 20 placed in the position A or the position B. In order to simplify the description, the distance from the eye E to the screen 20 placed in the position A or the position B is determined by measuring the horizontal distance from the eye E to the screen 20 placed in the position A or the position B. Chart images C1 to C4 schematically illustrate the sizes of the chart images on the screen 20. Each of ends of the apparatus 100 and the apparatus 101 is defined as a reference M for measuring installation distances.

Positions of the projection lenses 8 and 9 on the optical axis correspond to the size of the chart image (which relates to the test distance) and an image forming position of the chart image (which relates to the installation distance).

Strictly speaking, the installation distance is a distance through which the chart image is projected onto the screen 20, namely a distance between the chart disk 4 and the screen 20. However, a distance between the reference M and the chart disk 4 is a little over 10 cm, while the installation distance is the order of 3 to 6 m. Therefore, it causes no substantial problems in considering that the reference M and the chart disk 4 are approximately equal in position.

In FIG. 2A, the installation distance between the screen 20 and the apparatus 101 is equal to the test distance between the screen 20 and the eye E. The relationship between the installation distance and the test distance is defined as Lo1=Lt1 or Lo2=Lt2.

The apparatus 100 has the two projection lenses, while the apparatus 101 has only one movable projection lens. The apparatus 101 forms (focuses on) a chart image on the screen 20 in accordance with the installation distance. As shown in FIG. 2A, the chart image is projected onto the screen at a fixed spread angle D101. The size of the chart image to be formed on the screen 20 is determined in accordance with the installation distance.

FIG. 2A is a schematic view. The projection lens of the apparatus 101 is moved on an optical axis, thereby forming the chart image on the screen 20. Therefore, strictly speaking, the spread angle D101 of the chart image projected by the apparatus 101 slightly varies depending on the installation distance. However, an amount of variation in the spread angle D101 is very small comparing to the installation distance. Therefore, the spread angle D101 may be considered to be approximately constant. The chart image C1 or C2 having the size which is proportional to the installation distance Lo1 or Lo2 is formed on the screen 20 placed in the position A or the position B. Here, the eye E can see the chart image C1 and the chart image C2 by substantially the same angle of sight.

Meanwhile, in FIG. 2B, the installation distance (Lo3 or Lo4) between the screen 20 and the apparatus 100 differs from the test distance (Lt1 or Lt2) between the screen 20 and the eye E. The relationship between the test distance and the installation distance is defined as Lt1<Lo3 or Lt2<Lo4. When projecting the chart image onto the screen 20 placed in the position A or the position B from the apparatus 100 under such conditions, the chart image C3 corresponding to the test distance Lt1 needs to be formed on the screen 20 in the same size as the chart image C1. Similarly, the chart image C4 corresponding to the test distance Lt2 needs to be formed on the screen 20 in the same size as the chart image C2.

Here, in the apparatus 100, the size of the chart image formed on the screen 20 is adjusted by moving the projection lenses 8 and 9. The chart image C3 is obtained by a light bundle Z3, while the chart image C4 is obtained by a light bundle Z4. Even though the size of the chart image C3 on the screen 20 is equal to the size of the chart image C1, a spread angle of the light bundle Z3 for obtaining the size of the chart image C3 differs from a spread angle of a light bundle ZE which is used when the eye E and the apparatus 100 are in a same position. When the test distance is changed, a spread angle of the light bundle Z4 corresponding to the test distance Lt2 differs from the spread angle of the light bundle Z3 corresponding to the test distance Lt1.

For adjusting the size of the chart image to be formed, a sample chart for size adjustment, which is predetermined in accordance with the test distance, is placed in the position of the screen 20, and an operator moves the projection lenses 8 and 9 so that the sample chart and the projected chart image become equal in size.

Regarding the apparatus 100 having the configuration described above, it is newly found that chart brightness presented to the examinee varies depending on the installation distance and the test distance. This is because, when making the size of the chart image C3 equal to the size of the chart image C1, an amount of reduction in the brightness resulting from increase in the installation distance from Lo1 to Lo3 is greater than an amount of increase in the brightness resulting from decrease in a projection magnification.

A description of how to adjust the chart brightness so that it falls within a predetermined reference range even when the installation distance and the test distance are changed is provided below. A reference range of chart brightness of the apparatus according to the present invention is 230±30 cd/m$^2$ (this reference range is much narrower than the range of the international standard for brightness). However, for general visual acuity testing, chart brightness is not limited to this reference range (230±30 cd/m$^2$). In the preferred embodiment of the present invention, the light intensity of the illumination light source 1 is adjusted so as to satisfy the reference range. The installation distance and the test distance are independently set within a range of 3 to 6 m.

First, in accordance with the installation distance and the test distance, the light intensity of the illumination light source 1 which makes the brightness fall within the reference range is determined. Installation distances and test distances with predetermined steps (steps of 0.5 m herein) are set. A driving current value (or voltage) flowing through the illumination light source 1 when the reference range of the brightness is satisfied is calculated and included in a correspondence table shown in FIG. 3. In FIG. 3, the installation distances are listed in a row, and the test distances are listed in a column. In addition, for combinations of the installation distances and the test distances, current values which makes the brightness fall within the reference range are listed in FIG. 3. FIG. 3 does not indicate any concrete values, but indicates only the format of the table. The current values to be set can vary depending on factors such as characteristics of the white LED used as the illumination light source 1. The correspondence table (correspondence data) including the current values to be set for changing the chart brightness is stored in the memory 75 that defines storage means of the control unit 70. The control unit 70 controls to call up the current value corresponding to the installation distance and the test distance set by the distance setting unit 71 from the memory 75 and changes an amount of the current which flows into the illumination light source 1.

Regarding the projection-type visual acuity testing apparatus 100 having the configuration described above, installation of the apparatus 100 and adjustment of the light intensity therein are described below. An examiner (operator) places the apparatus 100 in a position at a predetermined distance from the screen 20 (an installation distance of 5 m is used herein). The examiner then determines the test distance (4 m herein), changes positions of the projection lenses 8 and 9, and performs adjustment so as to project the chart image onto the screen 20. Considering the test distance, the examiner adjusts the size of the chart image formed on the screen 20 using the sample chart described above.

Next, the examiner rotates the installation distance setting knob 71a to set the installation distance to 5 m. The examiner also rotates the test distance setting knob 71b to set the test distance to 4 m. Based on the correspondence table stored in the memory 75, the control unit 70 controls to set a current value (adjustment value) corresponding to the set values set by the knobs 71a and 71b. When the installation distance or the test distance is set to a set value (e.g. 4.8 m) which does not coincide with any distances in the correspondence table, the control unit 70 assumes that the nearest distance in the correspondence table is set as the set value, and controls to set the current value accordingly. This enables the chart brightness to fall within the range of 230±20 cd/m$^2$.

Such adjustment of the light intensity allows the brightness of the chart image presented to the examinee to conform to the reference range regardless of the installation distance (the position of the apparatus 100 with respect to the screen 20) and the test distance (the position of the eye E with respect to the screen 20). Accordingly, it is possible to perform accurate visual acuity testing.

In the preferred embodiment of the present invention, the correspondence table shown in FIG. 3 or data equivalent to the correspondence table is stored in the memory 75, and the control unit 70 controls to call up the data; however it is not limited thereto. For example, a variable resistor may be connected to each of the installation distance setting knob 71a and the test distance setting knob 71b. Projection light intensity of the chart image may be adjusted by changing resistance values of the variable resistors based on rotation amounts of the knobs 71a and 71b.

Alternatively, the reference range of the brightness may be satisfied in conjugation with positions of the projection lenses 8 and 9 (the distance setting unit 71 does not need to be operated). For example, position detection means (a position detection unit such as an encoder and a potentiometer) may be attached to each of the projection lenses 8 and 9. The control unit 70 calculates a test distance and an installation distance based on travel positions of the projection lenses 8 and 9 which are manually moved by the examinee, and controls to set a current value corresponding to the test distance and the installation distance.

Still alternatively, the projection lenses 8 and 9 may be moved by moving means (a driving unit such as an actuator). In this case, only by setting a test distance and an installation distance by the knobs 71a and 71b (the projection lenses 8 and 9 do not need to be manually moved), the control unit 70 controls the moving means to move the projection lenses 8 and 9, and a current value corresponding to the test distance and the installation distance is set.

In the preferred embodiment of the present invention, the test distance and the installation distance are set by the distance setting unit 71; however, it is not limited thereto. A distance between the apparatus 100 and the eye E and the installation distance may be set instead. In this case, a current value corresponding to the distance between the apparatus 100 and the eye E and the installation distance is set.

Further, in the preferred embodiment of the present invention, the control unit 70 controls the light intensity of the illumination light source 1; however, it is not limited thereto.

Since it is sufficient that the chart brightness on the screen 20 is adjusted, the light intensity of the illumination light source 1 may be fixed and the projection lenses 8 and 9 may be equipped with light intensity diaphragms. For example, the light intensity diaphragms may be moved on the optical axis, or apertures of the light intensity diaphragms may be changed. With such a configuration, color of the chart image does not change along with a change in the brightness even when an illumination light source whose color temperature tends to change depending on the light intensity is used as the illumination light-source 1. Therefore, it is possible to perform accurate testing.

Additionally, instead of the light intensity diaphragms, a member which has a light shielding portion and a light transmitting portion and is capable of changing a light transmitting ratio may be provided in the projection optical system.

In the preferred embodiment of the present invention described above, the chart brightness is substantially constant regardless of the installation distance and the test distance. Additionally, a configuration for making fine adjustment of the chart brightness may be added to the preferred embodiment. This is because variations in the chart brightness have an effect on test results, and thus there may be cases where the fine adjustment of the chart brightness is performed at an optician's shop or an ophthalmology clinic. For example, a knob for fine adjustment which performs fine adjustment of the light intensity may be provided on the distance setting unit 71, and the chart brightness may be increased or decreased within a range of several tens of $cd/m^2$. Accordingly, if the brightness of the chart image of an existing visual acuity testing apparatus slightly differs from that of the apparatus according to the present invention, it is possible to make the test results of the apparatus according to the present invention compatible to those obtained by the existing apparatus. Additionally, a change in the light intensity due to aging degradation of the illumination light source 1 can be compensated.

In addition, instead of providing the knob for fine adjustment, the installation distance setting knob 71*a* and/or the test distance setting knob 71*b* may be rotated in only one step so as to adjust the projection light intensity of the chart image.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A visual acuity testing apparatus (100) which projects an image of a chart for visual acuity testing onto a screen (20), the apparatus comprising:
    a projection optical unit including
        a disk (4) whereon the chart is placed,
        an illumination light source (1), and
        variable projection lenses which include a plurality of projection lenses (8, 9) movable in a direction of an optical axis which are moved so as to change an image-forming position and an image size of the chart image;
    an input unit (71) into which an installation distance which defines a distance between the screen and the visual acuity testing apparatus and a test distance which defines a distance between the screen and an examinee are inputted;
    a projection lens driving unit which moves the variable projection lenses based on the installation distance and the test distance inputted into the input unit; and
    a light intensity adjusting unit (70, 71) which adjusts light intensity based on the installation distance and the test distance so that brightness of the chart image falls within a predetermined reference range.

2. The visual acuity testing apparatus according to claim 1, wherein the reference range of the brightness is narrower than an allowable range of the international standard for brightness.

3. The visual acuity testing apparatus according to 1, wherein the reference range of the brightness is a range of $\pm 20$ $cd/m^2$ with respect to certain brightness.

4. The visual acuity testing apparatus according to claim 1, further comprising a position detection unit which detects travel positions of the projection lenses, wherein
    the light intensity adjusting unit adjusts the brightness of the chart image in accordance with the installation distance and the test distance calculated based on the travel positions of the projection lenses.

5. The visual acuity testing apparatus according to claim 1, wherein the light intensity adjusting unit includes a memory (75) which stores adjustment values of the light intensity which is predetermined in accordance with installation distances and test distances and adjusts the light intensity based on an adjustment value corresponding to the installation distance and the test distance inputted into the input unit, the adjustment value stored in the storage means.

6. The visual acuity testing apparatus according to claim 1, wherein the light intensity adjusting unit includes one of a control circuit which adjusts the light intensity of the illumination light source and a variable resistance circuit which adjusts the light intensity of the illumination light source.

* * * * *